United States Patent [19]

Maass

[11] 4,056,097
[45] Nov. 1, 1977

[54] CONTACTLESS STIMULUS TRANSDUCER

[76] Inventor: Joachim Adolf Maass, 179 East Maxwell St., Lexington, Ky. 40508

[21] Appl. No.: 666,646

[22] Filed: Mar. 15, 1976

[51] Int. Cl.$^2$ .............................................. A61N 1/42
[52] U.S. Cl. ........................ 128/1.5; 128/1 C; 128/82.1; 128/419 R; 128/419 C; 128/419 F
[58] Field of Search ............... 128/1.5, 1.3, 1 C, 82.1, 128/404, 405, 410, 411, 413, 419 R, 419 F, 419 C

[56] References Cited

U.S. PATENT DOCUMENTS

| 2,404,283 | 7/1946 | Gieringer | 128/405 |
| 3,095,880 | 7/1963 | Haagensen | 128/411 |
| 3,337,776 | 8/1967 | Elmi | 128/1.3 X |
| 3,658,051 | 4/1972 | MacLean | 128/1.5 |
| 3,841,306 | 10/1974 | Hallgren | 128/1.5 |
| 3,890,953 | 6/1975 | Kraus et al. | 128/1.5 |
| 3,915,151 | 10/1975 | Kraus | 128/1.5 |

FOREIGN PATENT DOCUMENTS

| 744,073 | 4/1933 | France | 128/1.5 |
| 631,377 | 12/1927 | France | 128/1.5 |
| 143,715 | 8/1903 | Germany | 128/1.5 |

Primary Examiner—Robert W. Michell
Assistant Examiner—Lee S. Cohen
Attorney, Agent, or Firm—Dennison, Dennison, Meserole & Pollack

[57] ABSTRACT

A contactless stimulus transducer which induces a stimulus current into a living system by means of a changing magnetic field which is produced by an electric field winding on a ferro-magnetic core which consists of two similarly or nearly similarly shaped pole pieces whose lateral boundary surfaces have equidirectional curvatures and whose concave sides face each other.

8 Claims, 2 Drawing Figures

CONTACTLESS STIMULUS TRANSDUCER

The present invention relates to stimulus transducers and more particularly to contactless stimulus transducers which induce a stimulus current into a living system by means of a changing magnetic field which is produced by an electric field winding on a ferro-magnetic core.

The stimulation of electrically excitble tissue is a method which has met with gaining acceptance due to its wide applicability in diagnostic and therapeutic fields. Typically, stimulation is achieved by means of externally applied or implanted electrodes. When using stimulating devices with galvanic electrodes difficulties arise, particularly when skin electrodes are to be used for the stimulation of neural or neuro-muscular tissue.

Relatively high current densities are frequently necessary to achieve physiologically effective stimulating currents in the deeper tissue layers. Often, this problem is aggravated by the fact that such structures exhibit a pathologically reduced excitability.

Intervening tissue layers with alternately high and low electrical conductivity convert most of the supplied electrical energy into heat. Layers of low electrical conductivity act as resistances between electrode and the tissue to be stimulated while the layers with high conductivity act as shunt by-passes.

The anatomically as well as electrically non-homogeneous structure of biological systems results in a non-linear relation between resistance and geometric distance from the electrode, creating a highly contorted field distribution which is difficult to predict.

These are the reasons for pain sensations which are elicited frequently long before the attempted stimulating effect is achieved. Stimulating through needle electrodes improves the situation electrically but tends to change the pain stimulus from an electrical to a mechanical one.

Electrical stimulation of sensory pathways can also be used to modify pain sensations in such a way that any remaining sensory information is no longer experienced as pain.

This avoids irreversible and risky surgical operations on the spinal cord as well as the possible systemic damages and drug addiction caused by chemically produced anesthesia and analgesia. Mere implantation of galvanic electrodes poses a certain risk and is saddled with the disadvantages of all the galvanic contacting methods.

To eliminate the problems associated with galvanic electrodes a contactless method of electrical stimulation has been proposed. It is based on the well-known fact that an electromotive force is induced in an electrically conductive medium which is placed in a changing magnetic field. To achieve the desired effect it is only necessary to expose the tissue to be stimulated to a powerfully changing magnetic field.

It is known that a magnetic field, produced by a current-carrying conductor loop, is strongest inside the loop and near the conductor. If an approximately cylindrical object, e.g., a human head, is positioned inside such a current conducting loop, it would occupy the area of the strongest field concentration. However, the largest electromotive force would still be produced near the conductor, i.e., in the superficial layers of the head. Some experiments have been made to try this method on human subjects.

Yet, for purposes of electroanesthesia it would be more desirable to transfer the highest field concentration into the area of the spinal cord or the brain stem, i.e., into the deeper biological structures. Otherwise, adjacent tissue will also be stimulated, perhaps even stronger than the desired structure. This situation would resemble that of galvanic stimulation.

More recently, inductive stimulators have become known which will concentrate the magnetic field in a specific space by means of an electromagnet with a ferro-magnetic core whose pole pieces are suitably shaped in order to achieve the desired effect. Their chief disadvantages are that the often very different shapes of their pole pieces and the heavy weight of their iron-core makes them unwieldy and that they cannot produce more than one predetermined field distribution, i.e., a stimulator which has been designed for the stimulation of structures inside the human head could not be used also for the stimulation of the spinal cord in the area of the thorax due to the vastly different shapes and sizes of these specimen.

Needed is therefore a stimulator which is as small as possible and at the same time as universally applicable as can be expected. The present invention fulfills this need.

An object of this invention is the provision of an inductive stimulator which is easy to use and handy to apply.

Another object is to provide for an inductive stimulator exhibiting the advantages mentioned before which can be adapted for the stimulation of almost all excitable tissue in various parts of the human body.

It is a further object of the invention to reduce the size and weight of the ferro-magnetic core to that of its essential elements, i.e., that of the pole pieces alone.

Still another object is to provide for pole pieces which produce the desired field distribution in the gap while maintaining a constant magnetic induction throughout the pole pieces.

The invention meets these objects by providing for a ferro-magnetic core which consists of two similarly or nearly similarly shaped pole pieces whose lateral boundary surfaces have equidirectional curvatures, whose surface area is partly covered by insulated electrical field windings and whose concave sides face each other.

The centers of curvature of the lateral boundary surfaces of a pole piece may or may not coincide. Similarly, the radii of curvature of both lateral boundaries may or may not be the same. However, the boundary surfaces are always designed in such a way that they intersect along a vertical edge whose distance from the similar edge in the second pole piece can be made adjustable to achieve a desired field distribution.

Each pole piece has a similar vertical edge on its opposite end which is connected to the similar edge of the other pole piece by a hinged or sliding linkage. This facilitates the adjustment. Near the movable pole piece connection an abrupt change in the radius of curvature of the inner surfaces may be utilized to achieve a higher field concentration in a space closer to the linkage end of the pole piece.

In addition to the movability of the pole pieces also the field winding can be altered by changing the number, the pitch and/or the locations of the turns. This allows to further optimize for a given application the distribution of the magnetic field between the pole pieces.

Thus, a particular design of a stimulator according to this invention may be used for many different applications such as electro-anesthesia or -analgesia, for stimulation of motor neurons, for accelerating bone, tendon or wound healing, for cardiac pace making or, perhaps, even for use as a contactless defibrillator.

The field windings of both pole pieces are wound and connected in such a way that the resulting magnetic fields are opposing each other, i.e., at any given time like magnetic polarities exist at the two pole-piece ends that are linked together and the opposite polarity exists at both of the free ends of the pole pieces.

It is apparent from this design of movable ferro-magnetic pole pieces with alterable and movable field windings that the invented stimulator is easy to handle and facilitates the production of a desired magnetic field distribution.

A pulse generator is used to power the field windings.

Further details of this invention as well as other objects and advantages thereof will be readily apparent from consideration of the following specifications relating to the annexed drawing in which.

Figure 1:
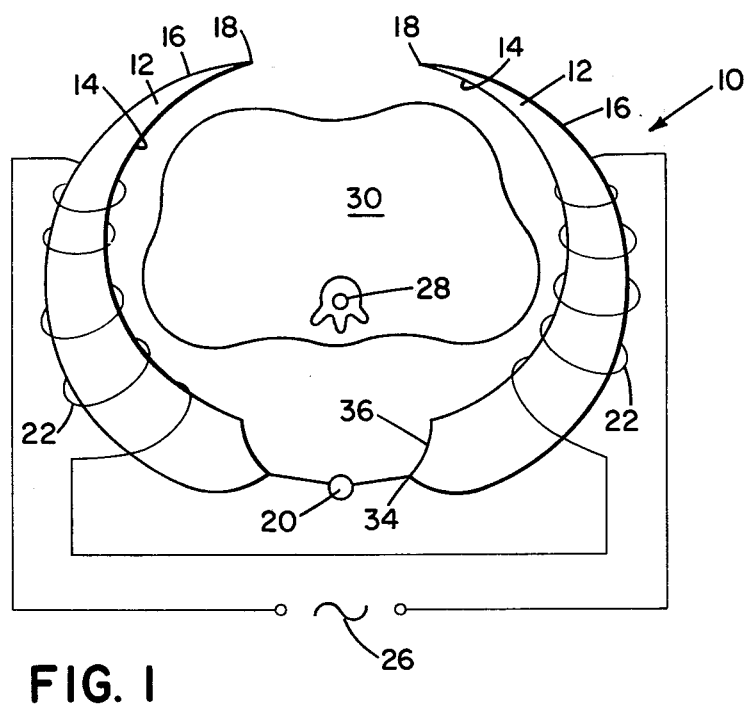
FIG. 1 is an embodiment of the invention used to stimulate the human spinal cord in the thoracic region.

Referring now to the drawings there is shown in FIG. 1 a stimulator 10 (which illustrates a preferred embodiment of the invention) which is stimulating the spinal cord 28 in the region of the thorax 30. The stimulator 10 consists of two similar pole pieces 12 whose lateral boundary surfaces include inner pole face 14, and outer surface 16, which are curved so as to completely or partially encircle the specimen to be stimulated. Surfaces 14 and 16 intersect at the vertical edge 18 with the curvatures of the inner surfaces having a smaller radii of curvature as shown in the illustrated embodiment. The result is a sickle-shaped appearance of the pole pieces 12.

In order to make the distance between edges 18 adjustable the opposite edges 34 are linked by hinge 20. Hence, pole pieces 12 are easily movable.

Edges 34 result from the intersecting surfaces 16 and pole faces 36 where the curvature of surface 36 may be different from that of either 14 or 16.

Insulated windings 22, wrapping parts of the pole pieces 12, can be used as current conductors which will produce magnetic fluxes emitted from the pole faces 14 and 36 of the pole pieces 12 to create magnetic fields of desired strength and distribution in the space between the pole pieces 12.

Directions and connections of winding 22 are such that the field produced by one pole piece 12 is opposing that of the opposite pole piece, i.e., at any given time surfaces 14 and 16, extending from field winding 22 towards edges 18 have an equal magnetic polarity in both pole pieces 12 while at the same given time surfaces 14, 16 and 36, extending from winding 22 towards hinge 20, have the opposite magnetic polarity in both pole pieces 12.

The stimulator is powered by a stimulus generator or source of current 26 of unspecified detail which may operate, e.g., by periodically discharging a capacitor into the field windings 22. The resulting sine-wave current is typically disconnected not later than at the first maximum (one quarter pi) of the sine wave. The stimulus current, induced in the specimen, then has the form of the first quarter of a cosine wave. This pulse shape has been shown experimentally to be particularly energy effective for stimulus applications.

Figure 2:
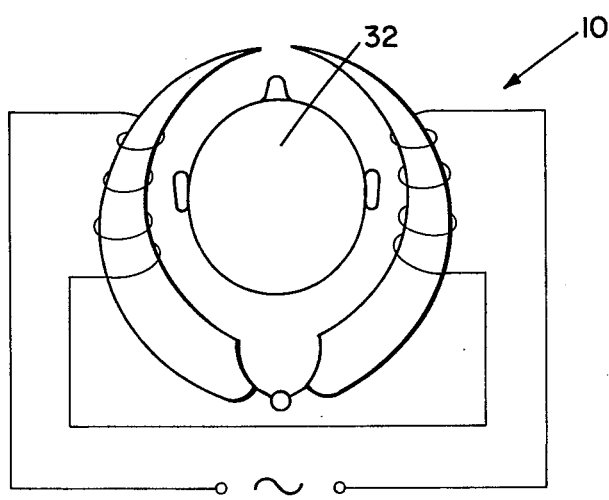
FIG. 2 is a similar embodiment of the invention used to stimulate structures in the human head.

Referring now to FIG. 2 of the drawing there is shown a similar stimulator 10 which is now used to stimulate structures in a human head 32. All the specifications and details are the same as in FIG. 1.

The embodiments of the invention in which an exclusive property or privilege is claimed are defined as follows:

1. Apparatus for stimulating a biological specimen, comprising at least two ferro-magnetic pole pieces, means for positioning said pole pieces in operative relation to said biological specimen, each of said pole pieces having an outer boundary surface of predetermined curvature and an inner curved surface intersecting the outer surface at opposite ends of the pole piece, said inner curved surfaces of the pole pieces confronting each other in at least partially encircling relation to the biological specimen to define a stimulus zone, a field winding mounted on each of said pole pieces intermediate the opposite ends thereof, a source of energizing current, and means connecting said source to the field windings for generating opposing magnetic fields extending from the inner surfaces of the pole pieces into the stimulus zone.

2. The combination of claim 1, wherein said inner surface of each of the pole pieces is formed by flux emitting faces of different curvature intersecting intermediate the opposite ends of the pole pieces.

3. The combination of claim 2, wherein said positioning means comprises means pivotally interconnecting the pole pieces at the ends thereof adjacent to the smaller of the flux emitting faces for dimensionally adjusting the stimulus zone.

4. The combination of claim 3, wherein the adjacent ends of the pole pieces are of the same magnetic polarity and said energizing current is time varied to produce changing magnetic fields.

5. The combination of claim 4, wherein each of the pole pieces has a cross-section between the inner and outer surfaces dimensioned to maintain a substantially constant magnetic induction between said opposite ends.

6. The combination of claim 1, wherein the adjacent ends of the pole pieces are of the same magnetic polarity and said energizing current is time varied to produce changing magnetic fields.

7. The combination of claim 1, wherein each of the pole pieces has a cross-section between the inner and outer surfaces dimensioned to maintain a substantially constant magnetic induction between said opposite ends.

8. The combination of claim 1, wherein the curvatures of the inner and outer surfaces of each pole piece have different radii of curvature.

* * * * *